United States Patent [19]

Enomoto

[11] 4,047,817
[45] Sept. 13, 1977

[54] PHOTOGRAPHIC COLOR DENSITOMETER CHECK PLATE

[75] Inventor: Hirobumi Enomoto, Minami-ashigara, Japan

[73] Assignee: Fuji Photo Film Co., Ltd., Minami-ashigara, Japan

[21] Appl. No.: 507,113

[22] Filed: Sept. 18, 1974

[30] Foreign Application Priority Data

Sept. 18, 1973 Japan .......................... 48-108903[U]

[51] Int. Cl.² .............................................. G01J 3/46
[52] U.S. Cl. .................................. 356/175; 350/317; 350/318; 356/173; 356/189; 356/194; 356/256
[58] Field of Search ....................... 350/311, 316–318; 355/32, 35, 38, 71; 356/186, 175, 189–194, 202, 203, 256

[56] References Cited

U.S. PATENT DOCUMENTS 2,809,552  10/1957  Ciavola ................................ 356/175
3,685,900  8/1972  Kirby ............................ 356/175 UX Primary Examiner—John K. Corbin
Assistant Examiner—F. L. Evans
Attorney, Agent, or Firm—Sughrue, Rothwell, Mion, Zinn and Macpeak

[57] ABSTRACT

A density check plate comprising a support having thereon a plurality of light absorbing filters, each of which has a light transmission limit wavelength at a different spectral wavelength and which completely and sharply absorbs light of a wavelength shorter than the wavelength of the light transmission limit wavelength.

4 Claims, 4 Drawing Figures

PHOTOGRAPHIC COLOR DENSITOMETER CHECK PLATE

BACKGROUND OF THE INVENTION

1. Field of the Invention

This invention relates to improvements in density check plates for checking the variation of the spectral characteristics of a densitometer.

2. Description of the Prior Art

Photographic color densitometers are generally provided with spectral filters for the three colors, red, green, and blue (hereinafter referred to as R, G, and B) of a color photosensitive material, or filters matched in visual density to measure the density of the three colors, R, G, and B, and the transmission density. The density value of te color photosensitive material to be measured greatly depends upon the characteristics of the spectral filters used in the photographic color densitometer. Accordingly, in the routine use of photographic densitometers, it is necessary to always check the density value so as to avoid a variation in the spectral characteristics of all optical systems in a device. This includes measuring the spectral filters.

For this reason, a density check plate employing six kinds (for high density and for low density of each color, R, G, and B; i.e., two kinds for each color), with each color, R, G, and B, of color plates which greatly vary in the value of the spectral density in the vicinity of the dominant wavelength of the three-colors, R, G, B spectral filter is generally used. The "Check Plaque" (product name) of the Eastman Kodak Co. is one example of such a density check plate.

The principle of the check plate as described above will be described with reference to FIG. 1. First, in the event a dye, for example, cyan, magenta, yellow recording on the photosensitive material, having a spectral density distribution $D_\lambda$ is measured with the use of a photographic color densitometer using a spectral filter having the spectral characteristic $A_\lambda$, a porton (hatched portion) in which both curves overlap is measured as a density value. However, if the characteristic $A_\lambda$ of the spectral filter should be changed into a characteristic as indicated at $B_\lambda$ due to a time variation (the time variation of the spectral filter is generally considered to be where the dominant wave-form is displaced and where more break-through occurs at the high density portion), the measured value greatly varies as may be seen clearly from the difference in the area of the hatched portion. The difference in the measured value becomes greater with the variation in the spectral characteristic of the dye in the vicinity of the dominant wavelength (435.8, 546.1, and 643.8 nm according to ASA Standards) of the three-color spectral filter increases. This makes it easy to check the variation in the spectral charcteristics of the spectral filter. Therefore, it is desirable to select a color plate having great variation in spectral characteristics to serve as a density check plate for the photographic color densitometer.

However, in a density check plate manufactured in a manner as described above, when the spectral characteristic of the spectral filter used in the photographic color densitometer varies, the density of the density check plate varies greatly due to the characteristic of the spectral filter, and as a result the same density check plate cannot be used.

SUMMARY OF THE INVENTION

It is therefore an object of this invention to provide a color densitometer check plate which overcomes the disadvantages noted above. The present invention provides a density check plate utilizing filters (sharp filters) which completely absorb a series of short wavelength sides having the spectral characteristics as shown in FIG. 2.

Accordingly, this invention provides a density check plate comprising a support having thereon a plurality of light absorbing filters, each of which has a light transmission limit wavelength at a different spectral wavelength and which completely and sharply absorbs light of a wavelength shorter than the wavelength of the light transmission limit wavelength.

In describing the invention in detail, reference will be made to the accompanying drawings.

DESCRIPTION OF THE PREFERRED EMBODIMENTS

Figure 1:
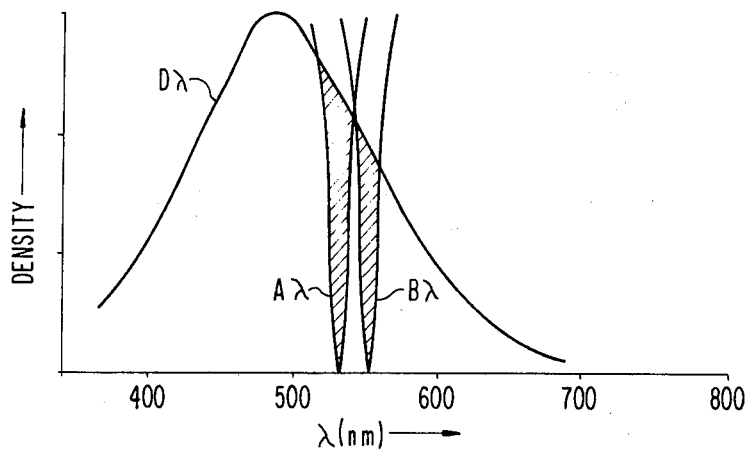
FIG. 1 illustrates the principle where the density of a dye is measured with the use of spectral filters.
Figure 2:
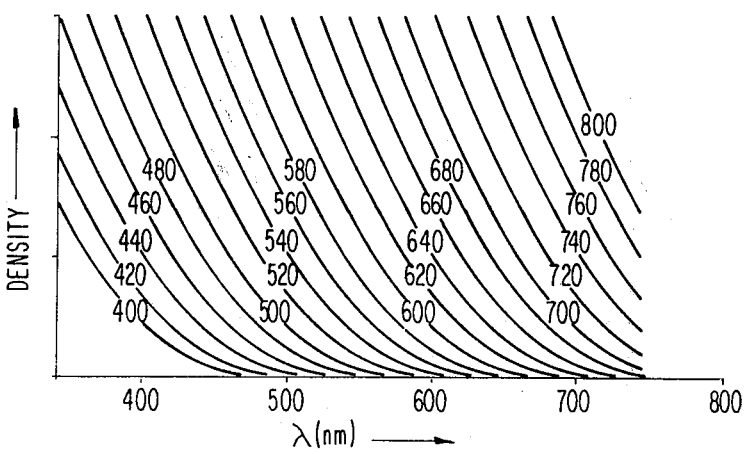
FIGS. 2 and 4 are graphs showing characteristic curves of a series of sharp filters in accordance with the present invention.

Referring now to FIG. 2, spectral characteristic curves of twenty-one sharply cut filters are shown, and the numerals noted therein designate transmission limit wavelengths of the filters. The transmission limit wavelength is shown at the mid-point of the wavelength corresponding to 5% and 72% of the curves of the transmission factor of the filters. Sharply cut filters having transmission limit wavelengths as generally shown in FIG. 2 are defined by Japanese Industrial Standard JIS B-7113.

Figure 3:
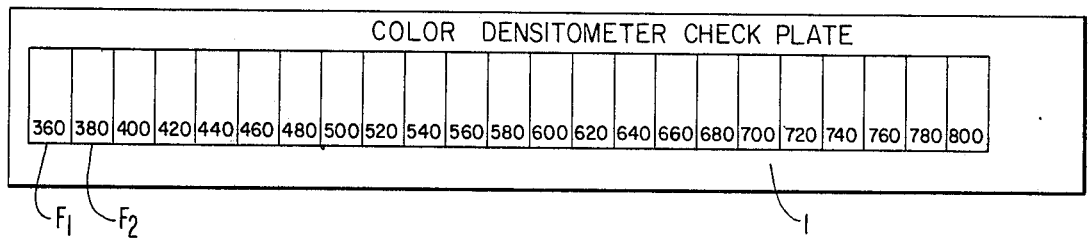
FIG. 3 shows a color densitometer check plate.

FIG. 3 is a plan view showing a preferred embodiment of a color densitometer check plate 1 according to the present invention. Within plate 1 is juxtaposed sharp filters $F_1$, $F_2$... over the wavelength range from 360 nm to 800 nm which absorb light in the short wavelength sides with the transmission limit wavelength difference between the filters being 20 nm. For the density check plate for color photographic densitometers, elements which can be used merely require the absorption of the short wavelength relative to the wavelength range as noted above. Color glass filters having good durability are often used because they are inexpensive, but these elements are not particularly limited to color glass filters.

Figure 4:
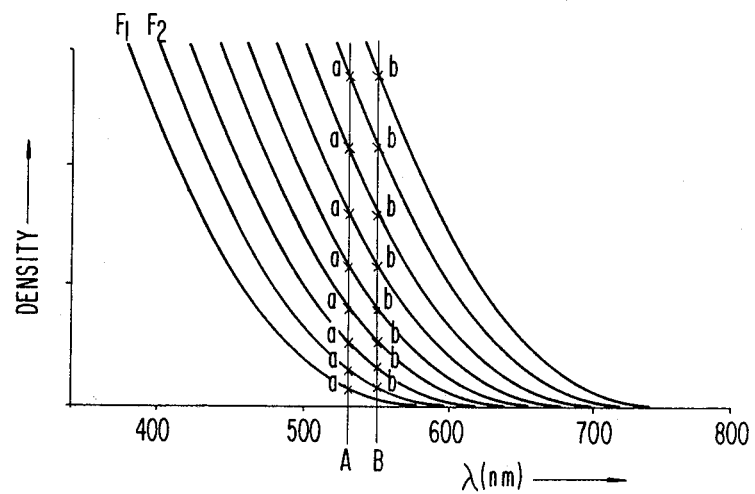

In the event the density check plate 1 as described above is used, even a densitometer using spectral filters different in dominant wavelength can have any of a series of sharp filters F used to check the density of colors, R, G, and B. This will be described with reference to FIG. 4 showing the characteristic curves of sharp filters $F_1$, $F_2$... Reference character A designates a dominant wavelength of the spectral filters of the densitometer and B designates a dominant wavelength displaced due to the time variation of the filters. In this case, substantially the same value of density can be used as a check point by varying the density check point from (a) to (b). In the density check plate 1 of the present invention, the sharp filters can be juxtaposed in such a way that the spacing of the transmission limit wavelength narrows particularly only in the vicinity of the dominant wavelength of the R, G, B color resolving filters.

While the check plate has been described for use with a photographic color densitometer, it will readily be understood that the present invention is not limited to the measurement of density of color photosensitive media but includes densitometers which are used to measure the color density of a dye, a solution of a dye, etc.

The present invention provides a great effect for practical use in the provision of a density check plate applicable even for densitometers utilizing any form of spectral filters by the stepwise juxtaposition of a series of sharp filters.

While the invention has been described in detail and with reference to specific embodiments thereof, it will be apparent to one skilled in the art that varius changes and modifications can be made therein without departing from the spirit and scope thereof.

What is claimed is:

1. A photographic color densitometer check plate comprising a support having thereon a plurality of light absorbing filters, each of which has a light transmission limit wavelength at a different spectral wavelength and which comletely and sharply absorbs light of a wavelength shorter than the wavelength of the light transmission limit wavelength said light transmission limit wavelength being defined as the mid-point of the wavelength corresponding to 5% and 72% of the curves of the transmission factor of the filters, said filters having light transmission limit wavelengths which are equally spaced over the wavelength region of the densitometer check plate.

2. The photographic color densitometer check plate of claim 1, wherein the wavelength region of the densitometer check plate varies from about 360 nm to 800 nm.

3. The photographic color densitometer check plate of claim 1, wherein said filters are glass filters.

4. A photographic color densitometer check plate comprising a support having thereon a plurality of light absorbing filters, each of which has a light transmission limit wavelength at a different spectral wavelength and which completely and sharply absorbs light of a wavelength shorter than the wavelength of the light transmission limit wavelength, wherein the difference between the light transmission limit wavelengths near the wavelengths corresponding to red, green and blue light is less than the difference in separation of th filters having light transmission limit wavelengths away from the wavelengths of light corresponding to red, green and blue light.

* * * * *